(12) United States Patent
Brown et al.

(10) Patent No.: US 7,123,690 B1
(45) Date of Patent: Oct. 17, 2006

(54) RADIOLOGICAL MARKER DEVICE

(75) Inventors: Linda S. Brown, 404 N. Rock Glen Rd., Baltimore, MD (US) 21229; Alaina Lee Tillage, Sparrows Point, MD (US)

(73) Assignee: Linda S. Brown, Owings Mills, MD (US)

( * ) Notice: Subject to any disclaimer, the term of this patent is extended or adjusted under 35 U.S.C. 154(b) by 38 days.

(21) Appl. No.: 10/938,912

(22) Filed: Sep. 10, 2004

(51) Int. Cl.
*H05G 1/28* (2006.01)

(52) U.S. Cl. ...................................... 378/165; 378/162

(58) Field of Classification Search ................ 378/165, 378/162, 163, 166, 65; 602/58
See application file for complete search history.

(56) References Cited

U.S. PATENT DOCUMENTS

| | | | |
|---|---|---|---|
| 4,429,412 A | 1/1984 | Pierce et al. ................ 378/165 |
| 5,045,080 A | 9/1991 | Dyer et al. .................. 604/362 |
| 5,193,106 A | 3/1993 | DeSena ....................... 378/163 |
| 5,345,494 A * | 9/1994 | Willey ......................... 378/162 |
| 5,592,527 A | 1/1997 | Ray ............................. 378/165 |
| 6,160,870 A | 12/2000 | Jacobson ..................... 378/165 |
| 6,198,807 B1 * | 3/2001 | DeSena ....................... 378/165 |

* cited by examiner

*Primary Examiner*—Edward J. Glick
*Assistant Examiner*—Hoon Song
(74) *Attorney, Agent, or Firm*—Sturm & Fix LLP

(57) ABSTRACT

An x-ray marker device (10) for use on a sheet of x-ray film (100) in a diagnostic radiology environment wherein, the marker device (10) includes a radiologically transparent housing member (20) having a front face (22) provided with a decorative element (23) and a rear face (24) provided with means (25) for releasably securing the housing member (20) to the x-ray cassette (100) and a plurality of radiologically opaque indicator members (30) embedded within the housing member (20) wherein, the indicator members include a peripheral indicator member (31) a directional indicator member (32) and one or more technician identification indicator members (33).

12 Claims, 1 Drawing Sheet

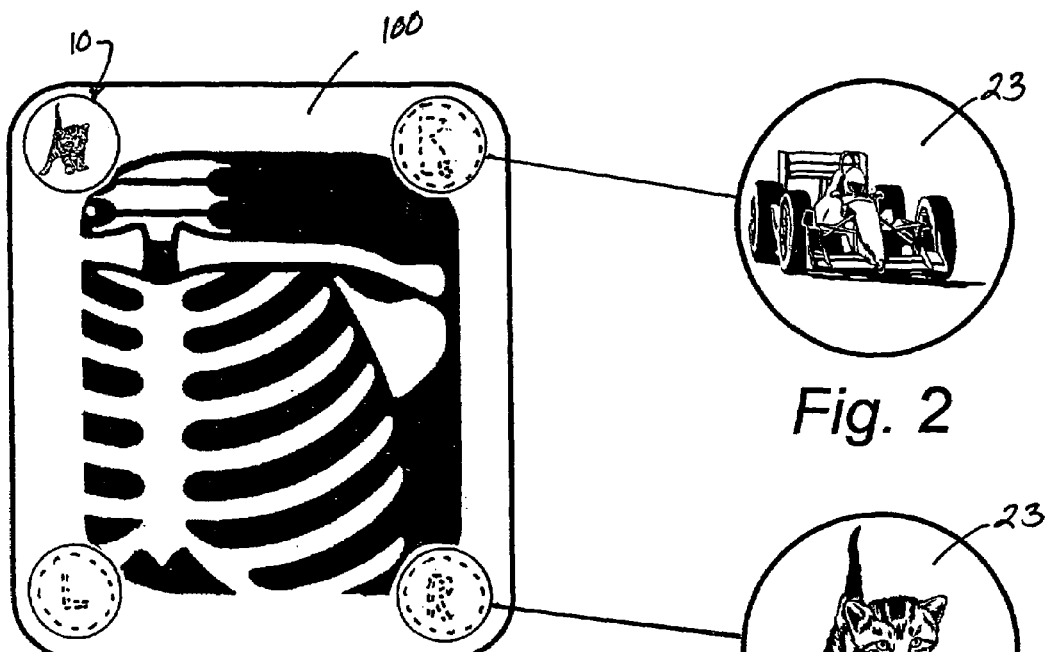
Fig. 1
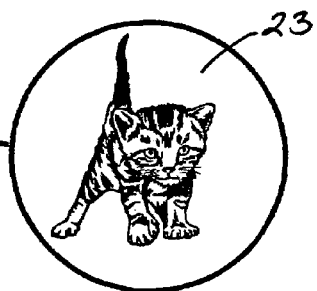
Fig. 2
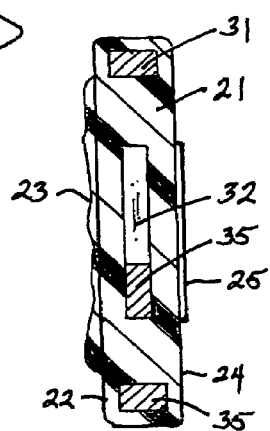
Fig. 3
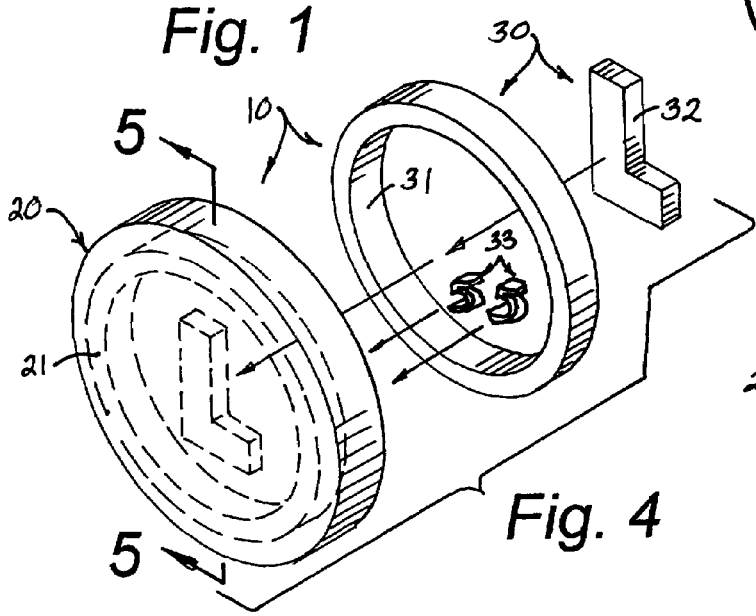
Fig. 4
Fig. 5
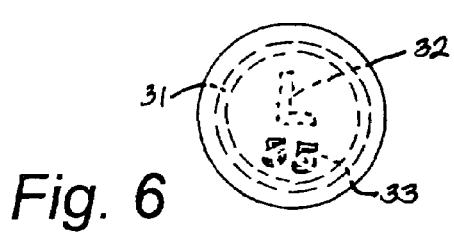
Fig. 6
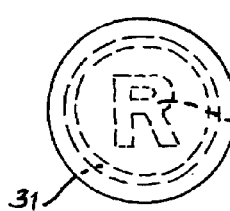
Fig. 7

RADIOLOGICAL MARKER DEVICE

CROSS REFERENCE TO RELATED APPLICATIONS

Not applicable.

BACKGROUND OF THE INVENTION

1. Field of the Invention

The present invention relates to the field of x-ray marking devices in general and in particular to an x-ray marker that is particularly well-suited to allay the fears of young children undergoing an x-ray procedure for the first time.

2. Description of Related Art

As can be seen by reference to the following U.S. Pat. Nos. 5,193,106; 6,160,870; 5,592,527; 4,429, 412; and, 5,045,080, the prior art is replete with myriad and diverse x-ray marker devices.

While all of the aforementioned prior art constructions are more than adequate for the basic purpose and function for which they have been specifically designed, they are uniformly deficient with respect to their failure to provide a simple, efficient, and practical x-ray marker device that satisfies all radiological safety requirements.

Most children undergoing pediatric x-ray procedures are already traumatized by injury and/or anxiety due to their unfamiliarity with this benign medical procedure and the more steps that can be taken to distract the child from the procedure and focus their attention elsewhere will lessen the trauma for the child and will improve the quality of the x-rays.

As a consequence of the foregoing situation, there has existed a longstanding need among radiologic technologists for a new and improved x-ray marker device that also has a decorative component on the x-ray marker to lessen the patient's anxiety level and to make the patient more receptive to the instructions of the radiologic technologist; and, the provision of such a device is the stated objective of the present invention.

BRIEF SUMMARY OF THE INVENTION

Briefly stated, the x-ray marker device that forms the basis of the present invention comprises in general a radiologically transparent housing member having a plurality of radiologically opaque indicator members embedded therein.

As will be explained in greater detail further on in the specification, the housing member has a front face provided with a decorative element that allows the x-ray technician to properly orient the indicator members embedded within the housing member.

Furthermore, the housing member has a rear face provided with a sticky, transparent element that allows the housing member to be releasably attached to an x-ray cassette wherein, the transparent element also allows a radiologic technologist to view indicia on the rear face of the housing member that correlates with one or more of the embedded indicator members.

In addition, the decorative element on the front face of the housing member serves the equally important function of giving the radio technologist a visual focal point for the child to concentrate on so that their attention will be temporarily diverted from any pain and/or anxiety that they are experiencing, as well as, giving the child a comforting reference point in which to orient their bodies in response to verbal instructions from the radio technologist.

BRIEF DESCRIPTION OF THE SEVERAL VIEWS OF THE DRAWINGS

These and other attributes of the invention will become more clear upon a thorough study of the following description of the best mode for carrying out the invention, particularly when reviewed in conjunction with the drawings, wherein:

FIG. 1 is a front plan view of a sheet of x-ray film and potential placement sites for the x-ray marker device of this invention;

FIGS. 2 and 3 show representative examples of the decorative elements that may be employed on the front face of the housing member;

FIG. 4 is an exploded perspective view of the housing member and the embedded indicator members;

FIG. 5 is a cross-sectional view taken through line 5—5 of FIG. 4;

FIGS. 6 and 7 show representative examples of typical indicator members that would be embedded within the housing member.

DETAILED DESCRIPTION OF THE INVENTION

As can be seen by reference to the drawings, and in particular to FIG. 4, the x-ray marker device that forms the basis of the present invention is designated generally by the reference number 10. The marker device 10 comprises a radiologically transparent housing member 20 and a plurality of radiologically opaque indicator members designated generally as 30 embedded within the housing member 20. These structural components will now be described in seriatim fashion.

As can best be seen by reference to FIGS. 4 and 5, the housing member 20 is fabricated from a radiologically transparent material 21 such as plastic or the like that allows x-rays to pass through the housing member 20 onto a sheet of x-ray film 100.

In addition, the housing member 20 has a front face 22 provided with a decorative element 23 and a rear face 24 provided with a transparent layer of tacky material 25 wherein, the purpose and function of the decorative element 23 and the layer of tacky material 25 will be described in greater detail further on in the specification.

Still referring to FIGS. 4 and 5, it can be seen that the radiologically opaque indicator members 30 include a peripheral indicator 31 that surrounds a directional indicator 32 and one or more technician identifying indicators 33 wherein, all of the indicator members 30 are fabricated from a radiologically opaque material 35 such as metal or the like that will prevent x-rays from passing through the x-ray film 100.

As shown in FIGS. 4, 6, and 7, the peripheral indicators 31 generally conform to the outer periphery of the housing member 20 and surround the directional indicators 32 which comprise the letters "L" and "R" representing "left" and "right" respectively. Furthermore, the technologist identifying indicators 33 would be much smaller in size than the directional indicators 32 and would be alpha/numeric in configuration so that doctors or radiologists reading the exposed x-ray film would not only have directional information available, but would also know the identity of the radiologic technologist that conducted the x-ray procedure.

Turning now to FIGS. 1 through 3, it can be seen that the decorative elements 23 have different visual themes chosen to appeal to different patients according to their age and sex wherein, the image on the decorative element 23 is aligned with the underlying directional indicator member 32 embedded within the housing member 20.

Furthermore, either the front face 22 or the rear face 24 of the housing member 20 is provided with printed indicia corresponding to the directional indicator member 32 contained within the housing 20 so that the radiologic technologist will know whether to position a particular x-ray marker device 10 on either the right or the left hand side of the x-ray film 100 and, in those instances when the indicia is imprinted on the rear face 24 of the housing member 20, the layer of tacky material 25 should be transparent as to not obscure the printed indicia.

Although only an exemplary embodiment of the invention has been described in detail above, those skilled in the art will readily appreciate that many modifications are possible without materially departing from the novel teachings and advantages of this invention. Accordingly, all such modifications are intended to be included within the scope of this invention as defined in the following claims.

Having thereby described the subject matter of the present invention, it should be apparent that many substitutions, modifications, and variations of the invention are possible in light of the above teachings. It is therefore to be understood that the invention as taught and described herein is only to be limited to the extent of the breadth and scope of the appended claims.

We claim:

1. An x-ray marker device for x-ray film wherein, the x-ray marker device comprises:
   a housing unit-member fabricated from radiologically transparent material and having a front face provided with a radiologically transparent decorative element and a rear face provided with means for releasably attaching the housing member to an x-ray cassette; and,
   at least one radiologically opaque indicator member located within said housing member and disposed in the same orientation as said decorative element wherein said at least one radiologically opaque indicator member has a different appearance than the radiologically transparent decorative element.

2. The device as in claim 1; wherein, said at least one radiologically opaque indicator member is a directional indicator member.

3. The device as in claim 2; including at least one additional indicator member disposed in a surrounding relationship with respect to said indicator member.

4. The device as in claim 3; wherein, said at least one additional indicator member is a peripheral indicator member.

5. The device as in claim 4; including at least one further indicator member in addition to the directional indicator member and the peripheral indicator member wherein, said one further indicator member is a technologist indicator member.

6. The device as in claim 5; wherein, directional indicia is selectively imprinted on one of the front and rear faces of the housing member.

7. The device as in claim 6; wherein, said means for releasably attaching the housing member to a sheet of an x-ray cassette comprises a layer of tacky material.

8. The device as in claim 7; wherein, said layer of tacky material is transparent.

9. The device as in claim 1; wherein, said at least one indicator member is embedded within the housing member.

10. The device as in claim 3; wherein, said at least one additional indicator member is embedded within the housing member.

11. The device as in claim 5; wherein, said at least one further indicator member is embedded within the housing member.

12. The device as in claim 5; wherein, all indicator members are embedded within the housing member.

* * * * *